United States Patent
Hong et al.

(10) Patent No.: US 11,406,628 B2
(45) Date of Patent: Aug. 9, 2022

(54) SUSTAINED-RELEASE TRIPTAN COMPOSITIONS AND METHOD OF USE THE SAME THROUGH SUBDERMAL ROUTE OR THE LIKE

(71) Applicants: Taiwan Liposome Co., Ltd, Taipei (TW); TLC Biopharmaceuticals, Inc., South San Francisco, CA (US)

(72) Inventors: Keelung Hong, South San Francisco, CA (US); Hao-Wen Kao, Taipei (TW); Yi-Yu Lin, Taipei (TW)

(73) Assignees: Taiwan Liposome Co., Ltd, Taipei (TW); TLC Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 16/766,127

(22) PCT Filed: Dec. 21, 2018

(86) PCT No.: PCT/US2018/067315
§ 371 (c)(1),
(2) Date: May 21, 2020

(87) PCT Pub. No.: WO2019/126766
PCT Pub. Date: Jun. 27, 2019

(65) Prior Publication Data
US 2020/0360362 A1 Nov. 19, 2020

Related U.S. Application Data

(60) Provisional application No. 62/608,898, filed on Dec. 21, 2017.

(51) Int. Cl.
*A61K 31/454* (2006.01)
*A61K 9/127* (2006.01)
(Continued)

(52) U.S. Cl.
CPC ............ *A61K 31/454* (2013.01); *A61K 9/127* (2013.01); *A61K 31/404* (2013.01);
(Continued)

(58) Field of Classification Search
CPC .... A61K 31/454; A61K 47/28; A61K 31/404; A61K 9/127; A61K 31/422;
(Continued)

(56) References Cited

U.S. PATENT DOCUMENTS

| 5,520,639 | A | * | 5/1996 | Peterson | ................. | A61M 5/30 |
| | | | | | | 604/140 |
| 2004/0071770 | A1 | * | 4/2004 | Smith | .................... | A61K 33/30 |
| | | | | | | 424/450 |

(Continued)

FOREIGN PATENT DOCUMENTS

| WO | 2005/048986 A1 | 6/2005 |
| WO | 2017/005853 A1 | 1/2017 |

OTHER PUBLICATIONS

Villasmil-Sanchez, S., et al in Drug Development and Industrial Pharmacy, vol. 36, Issue 6, 2010, pp. 666-675.*

(Continued)

*Primary Examiner* — Gollamudi S Kishore
(74) *Attorney, Agent, or Firm* — Leason Ellis LLP

(57) ABSTRACT

Provided is a sustained-release triptan composition as a suitable depot formulation to carry a therapeutically effective amount of triptan for administration via subcutaneous or intramuscular injection. This sustained-release triptan composition is characterized by a high drug to phospholipid ratio and provides an improved pharmacokinetic profile in vivo. The sustained-release triptan composition is for use as a medicament in the treatment of migraine or cluster headache.

6 Claims, 1 Drawing Sheet

(51) Int. Cl.
*A61K 31/4025* (2006.01)
*A61K 31/404* (2006.01)
*A61K 31/4196* (2006.01)
*A61K 31/422* (2006.01)
*A61K 47/28* (2006.01)

(52) U.S. Cl.
CPC ...... *A61K 31/4025* (2013.01); *A61K 31/4196* (2013.01); *A61K 31/422* (2013.01); *A61K 47/28* (2013.01)

(58) Field of Classification Search
CPC ............ A61K 31/4196; A61K 31/4025; A61K 31/135; A61K 31/4045; A61K 9/0019
See application file for complete search history.

(56) References Cited

U.S. PATENT DOCUMENTS

| | | | | |
|---|---|---|---|---|
| 2004/0214899 | A1* | 10/2004 | Dearn | C07D 413/06 514/651 |
| 2007/0269502 | A1* | 11/2007 | Pliura | A61P 43/00 424/450 |
| 2010/0247629 | A1* | 9/2010 | Gabizon | A61K 31/704 424/450 |
| 2014/0249077 | A1* | 9/2014 | Chen | A61P 3/06 514/5.3 |
| 2014/0288154 | A1* | 9/2014 | Bumcrot | C12N 15/111 514/44 A |
| 2015/0030672 | A1* | 1/2015 | Li | A61K 9/1271 424/450 |
| 2015/0202156 | A1* | 7/2015 | Caponetti | A61K 9/14 424/489 |
| 2016/0074324 | A1* | 3/2016 | Yang | A61K 38/22 424/450 |
| 2018/0066049 | A1* | 3/2018 | Datar | C07K 16/00 |

OTHER PUBLICATIONS

Doctors Lounge-Forum Index-Neurology-Headaches, Dec. 16, 2006.*
Duquesnoy, C., et al in Euronpean Journal of Pharmaceutical Sciences, vol. 5, pp. 99-104, 1998.*
Visser W H et al., Treatment of migraine attacks with subcutaneous sumatriptan: first placebo-controlled study, CEPHALA, 1992, vol. 12, No. 5, pp. 308-313.
International Search Report and Written Opinion of corresponding International Application PCT/US2018/067315, dated Mar. 20, 2019.

* cited by examiner

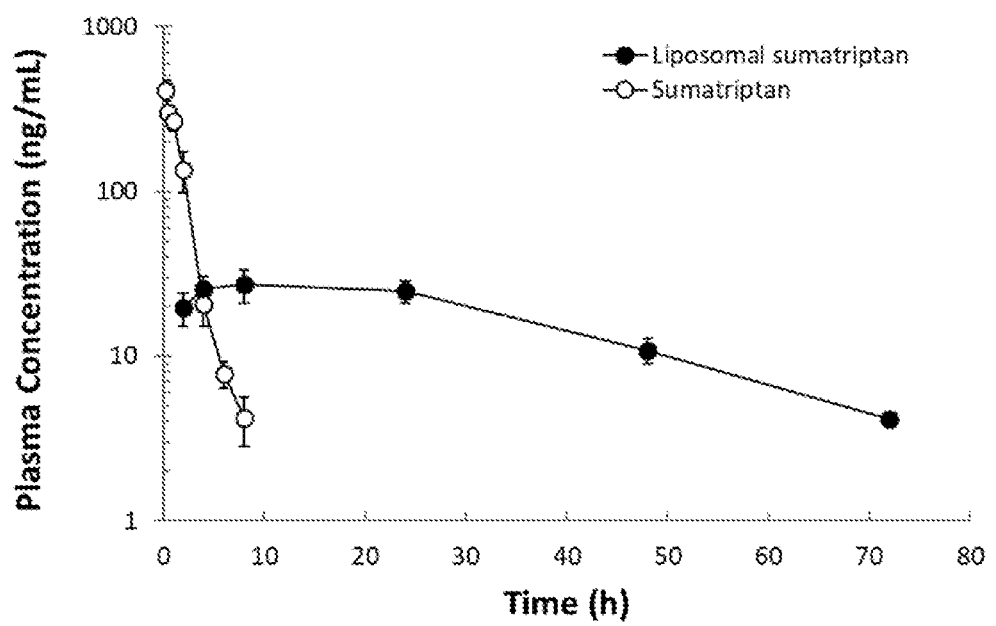

US 11,406,628 B2

SUSTAINED-RELEASE TRIPTAN COMPOSITIONS AND METHOD OF USE THE SAME THROUGH SUBDERMAL ROUTE OR THE LIKE

BACKGROUND

Technical Field

The present disclosure is directed to sustained-release triptan compositions, which are prepared by using the remote loading procedure to encapsulate the triptans into liposome, and for use in therapy.

Description of Related Art

Triptans have been developed and approved for the treatment of migraine. Sumatriptan is one example of triptan derivatives, specifically a 5-hydroxytryptamine$_{1B/1D}$ (5-HT$_{1B/1D}$) receptor agonist, employed as the primary drug in migraine and cluster headache therapies. There are several demonstrated treatment methods to administer sumatriptan to humans, including subcutaneous injection, oral tablet, intranasal spray, powder inhalation and transdermal patch. Among these dosage forms, the extent of absorption of sumatriptan by the subcutaneous injection at a dose of 6 mg is 96% to 97%, which is significantly higher than other routes. For example, the oral bioavailability of sumatriptan is 14%. Due to the rapid time to reach maximum plasma concentration, approximately 10 minutes, administration through subcutaneous injection exhibits the fastest onset of action compared to other routes. However, the half-life ($t_{1/2}$) of sumatriptan in human is only approximately 2 hours irrespective of route of administration, e.g., 2 hours for 6 mg of subcutaneous injection, 2 hours for 100 mg of oral tablet and 1.8 hours for 20 mg of intranasal administration (Drugs, 2000 December; 60(6):1259-87). This might be a major concern that the migraine recurrence rate within 24 hours or 48 hours of initial symptom resolution is about 40% when patients are treated with sumatriptan (*Expert Opin Pharmacother* 2012; 13(16):2369-80).

Liposomes as a drug delivery system are a successful technology and have been widely used for developing sustained-release formulations for various drugs. Drug loading with liposomes can be attained either passively (the drug is encapsulated during liposome formation) or remotely/actively (creating transmembrane pH- or ion-gradients during liposome formation and then the drug is loaded by the driving force generated from the gradients after liposome formation) (U.S. Pat. Nos. 5,192,549 and 5,939,096). However, it is unpredictable as to whether liposomes may increase drug carrying capacity or improve drug's pharmacokinetics even via the same administration route.

SUMMARY

The present disclosure provides sustained-release triptan compositions, for use in treating migraine and cluster headache, by subcutaneous or intramuscular administration, which comprises:
  a liposomal triptan has a mean particle size being not less than 100 nm; and comprises:
    one or more triptans entrapped by a trapping agent in a liposome, and the liposome includes one or more phospholipids; and
  wherein the molar ratio of the one or more triptans to the one or more phospholipids is not less than 0.1.

In another aspect, the present disclosure provides a method for treating migraine and cluster headache, which comprises:
  administering an effective amount of a sustained-release triptan composition by subcutaneous or intramuscular injection to a subject in need thereof,
  wherein the sustained-release triptan composition comprises the liposomal triptan according to the present disclosure,
  whereby a sustained release profile of the sustained-release triptan composition is demonstrated in vivo by an extended $t_{1/2}$ of triptan after administration of sustained-release triptan composition compared with that of unformulated triptan by the same injection route, either subcutaneous route or intramuscular route.

In one another aspect, the present disclosure provides a method of preparing the sustained-release sumatriptan composition which can serve as a depot to carry sufficient amount of drug in situ via single administration and then the drug is sustained-release from liposomes into systemic circulation to keep the plasma drug concentration continuously in the therapeutic range. This depot formulation offers superiority over conventional products by increasing the duration of action and reducing the dosage frequency. The liposomal sumatriptan is prepared by the remote loading method in a molar ratio of drug to the phospholipid(s) (D/PL) of at least 0.1 mole/mole with a mean particle size over 100 nm.

In accordance with the present disclosure, the sustained-release sumatriptan composition via subdermal injection route compared with their clinical available drugs in the same species display the improved pharmacokinetic profiles including a significantly prolonged half-life with a similar or lower dose-normalized maximum plasma concentration ($C_{max}$) exposure.

Other objectives, advantages and novel features of the disclosure will become more apparent from the following detailed description when taken in conjunction with the accompanying drawings.

BRIEF DESCRIPTION OF THE DRAWINGS

FIG. 1 is a graph showing the plasma concentration of sumatriptan in rats after subcutaneous injection of liposomal sumatriptan (closed circle) and unformulated sumatriptan (open circle).

DETAILED DESCRIPTION OF THE PREFERRED EMBODIMENTS

As employed above and throughout the disclosure, the following terms, unless otherwise indicated, shall be understood to have the following meanings.

As used herein, the singular forms "a", "an" and "the" include the plural reference unless the context clearly indicates otherwise.

All numbers herein may be understood as modified by "about," which means ±10% of the indicated range or value.

The term "treat" includes the reduction or amelioration of one or more symptoms of a triptan responsive state in a statistically significant manner compared to an untreated control. It also may include the prevention of the occurrence or reoccurrence of the triptan responsive state.

The term "triptan responsive states" includes migraines, familial hemiplegic migraines (with and without aura), chronic paroxysmal headaches, cluster headaches, migraine headaches, basilar migraines, and atypical headaches accompanied by autonomic symptoms, such as cyclic vomiting syndrome.

The term "effective amount" includes the amount of triptan which is effective to treat a particular triptan responsive state.

The term "subject" includes living organisms capable of having triptan responsive states (e.g., mammals). Examples of subjects include humans, dogs, cats, horses, cows, goats, rats and mice. In one embodiment, the subject is a human. In a further embodiment, the term includes subjects suffering from a triptan responsive state.

The term "drug to lipid ratio" or "drug to phospholipid ratio" is interchangeably used to refer to the molar ratio of triptan to the one or more phospholipids in liposomal triptan.

Liposome

Two triptans to be formulated with liposomal formulation had been mentioned, including sumatriptan (*Drug Dev Ind Pharm.* 2010; 36(6):666-75 and *J Liposome Res.* 2011; 21(1):55-9) and rizatriptan (*Drug Dev Ind Pharm.* 2008; 34(10):1100-10). The goal of both drug formulations with liposome using a passive loading method has been stated to improve the skin permeation as both formulations have been developed to be administrated via the transdermal route. Moreover, the in vivo characteristics of these formulations have not yet been reported to date. In this present disclosure, the aim of developing a sustained-release composition, e.g. a liposome, for administrating via subcutaneous or intramuscular route is to improve the pharmacokinetic profile of triptan drugs. This improvement will prolong the duration of a drug within a therapeutic window with a single administration and reduce the recurrence rate of migraine or cluster headache as well. Therefore, a sustained-release triptan composition is needed urgently in the field.

The term "liposome", "liposomal" and related terms as used herein are usually characterized by having an aqueous interior space sequestered from an outer medium by one or more bilayer membranes forming a vesicle. Bilayer membranes of liposomes are typically formed by lipids, i.e. amphiphilic molecules of synthetic or natural origin that comprise spatially separated hydrophobic and hydrophilic domains. Preferably, liposomes, in the practice of the present disclosure, include small unilamellar vesicles (SUVs), large unilamellar vesicles (LUVs) and multilamellar vesicles (MLVs), i.e., unilamellar liposomes and multilamellar liposomes having more than one lamina of lipid bilayer.

In general, liposomes comprise a lipid mixture typically including dialiphatic chain lipids, such as phospholipids, diglycerides, dialiphatic glycolipids, sphingolipids such as sphingomyelin and glycosphingolipid, sterol such as cholesterol and derivates thereof, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (D SPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanol amine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanola mine (PEG-DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). An exemplary phospholipid composition of use in the present disclosure comprises not more than 50 mole percentage of sterol, preferably cholesterol.

Remote Loading

The term "remote loading" as used herein is a drug loading method which involves a procedure to transfer drugs from the external medium across the bilayer structure of liposome to the internal medium by a concentration gradient. To create a concentration gradient, pH- or ion-gradients, the liposome is formed containing one or more than one trapping agent as the internal medium and the outer medium of the liposome followed by replacing with external medium, which can be achieved by several techniques, such as column separation, dialysis or centrifugation.

In accordance with the present disclosure, the liposome formed with trapping agent can be prepared by any of the techniques now known or subsequently developed for preparing liposomes. For example, the MLV liposomes can be directly formed by a hydrated lipid film, spray-dried powder or lyophilized cake of selected lipid compositions with trapping agent; the SUV liposomes and LUV liposomes can be sized from MLV liposomes by sonication, homogenization, microfluidization or extrusion.

Sustained-Release Triptan Composition and Liposomal Triptan

The sustained-release triptan compositions according to the present disclosure comprise a liposomal triptan. The liposomal triptan comprises: one or more triptans entrapped by a trapping agent in a liposome. The liposome includes multiple vesicles having a mean particle size not less than 100 nm. The vesicles are formed by one or more phospholipids. The molar ratio of the one or more triptans to the one or more phospholipids is not less than 0.1. The term "liposomal triptan" refers to a triptan being encapsulated in a liposome, which results in a maintained triptan concentration in circulation above therapeutic levels for prolonged periods in vivo. The liposomal triptan of the sustained-release triptan composition is prepared by the remote loading method which means that the liposome contains at least one trapping agent to entrap the triptan inside the liposome. An exemplary triptan according to the present disclosure is sumatriptan. Other triptans that may be used include, but are not limited to, naratriptan, eletriptan, frovatriptan, zolmitriptan, rizatriptan, and almotriptan. Exemplary trapping agents include, but are not limited to, ammonium sulfate, ammonium phosphate, ammonium molybdate, ammonium sucrose octasulfate, triethylammonium sucrose octasulfate and dextran sulfate. An exemplary sustained-release triptan composition comprises a triptan entrapped by a trapping agent in a liposome to form a liposomal triptan. This liposomal triptan includes one or more phospholipids, wherein the mean particle size of liposomal triptan is not less than 100 nm, 100 nm to 20 μm, 100 nm to 10 μm, 100 nm to 1000 nm, 100 nm to 500 nm, 100 nm to 400 nm, 100 nm to 300 nm, 100 nm to 250 nm, or 100 nm to 200 nm; and the molar ratio of the one or more triptans to the one or more phospholipids is no less than 0.1, alternatively from 0.1 to 100, from 0.1 to 50, from 0.1 to 40, from 0.1 to 30, or from 0.1 to 20. In addition, the liposomal triptan has a zeta potential ranging from −40 to 20 mV, alternatively ranging from −50 mV to 5 mV, −45 mV to 10 mV, −42 mV to 15 mV, −40 mV to 30 mV, −35 mV to 20 mV, −30 mV to 10 mV, −20 mV to 10 mV, −40 mV to 10 mV, −40 mV to 0 mV, −30 mV to 0 mV, −20 mV to 0 mV or −10 mV to 0 mV.

As a depot formulation, the pharmacokinetic study of sustained-release triptan composition after subcutaneous or intramuscular injections displays a significant extended-release profile of triptan in vivo. In an embodiment, the methods or the compositions of the present disclosure are advantageous over approved sumatriptan formulations, including those for subcutaneous, oral, intranasal and transdermal administrations, due to the prolonged half-life and reduced $C_{max}$ level.

For instance, Imitrex Nasal Spray is approved at a dose of 5, 10 or 20 mg of sumatriptan once in a human subject and may be repeated once after 2 hours. The maximum daily dose of Imitrex Nasal Spray is not more than 40 mg. Ayres et al. (*Xenobiotica*. 1996; 26(12):1273-82) and the NDA submitted package of Imitrex Nasal Spray (IMITREX® (sumatriptan) Nasal Spray New Drug Application (NDA) submitted package, GlaxoSmithKline, Application No.: 020626) have reported the $t_{1/2}$ of sumatriptan in female rats after intravenous administration and intranasal administration is 1.1 hour and 3.6 hours, respectively; the $C_{max}$/dose (normalization using sumatriptan succinate dosage) of sumatriptan in female rats after intravenous administration and intranasal administration is 508.6 ng/mL and 25 ng/mL, respectively.

The methods or compositions of the present disclosure can be described, at least in part, by using the pharmacokinetic parameters. The parameters reported include $t_{1/2}$, $C_{max}$, area under the plasma concentration time curve from time 0 to the last time point ($AUC_{0-t}$) and area under the plasma concentration time curve from time 0 and extrapolated to infinity ($AUC_{0-inf}$). As used herein, such parameters are measured according to Example 3 of the present disclosure.

In a further embodiment, in the present disclosure, the $C_{max}$/dose obtained from the liposomal sumatriptan group is 48-fold reduced compared to that obtained from the unformulated sumatriptan group via the same injection route. This pharmacokinetic profile of liposomal sumatriptan describes a lower drug exposure over a short period which has the potential to reduce medication related adverse events. Nevertheless, this present disclosure provides at least a 2-fold increase in sumatriptan dose, at least a 3-fold increase in sumatriptan dose, at least a 4-fold increase in sumatriptan dose, at least a 5-fold increase in sumatriptan dose, at least a 10-fold increase in sumatriptan dose, or at least a 15-fold increase in sumatriptan dose compared to the approved Imitrex Injectable in a clinical administration via the same route (subcutaneous).

According to the present disclosure, the term "unformulated active agent" refers to a composition comprising one or more active agents and one or more inert excipients. The active agents, for example, are triptans. The inert excipients are substances other than the active agents and have been appropriately evaluated for safety. In addition, the inert excipients enable the active agents to be applied to a patient in the aqueous solution form, and support the way and place of action without being active themselves, interaction with the active agents, or contributing to overall pharmacokinetics of the composition. Exemplary inert excipients include, but are not limited to, water for injection, saline solution, sucrose solution or various buffer solutions such as phosphate buffer solution, HEPES buffer solution, citrate buffer solution and histidine buffer solution.

In some embodiments, the $t_{1/2}$ obtained from the liposomal sumatriptan group (18.7 hours) is 17-fold extended compared to that obtained from the unformulated sumatriptan group (1.1 hours) via the same administration route. Due to the interspecies differences in the absorption, distribution, metabolism, and excretion of the sumatriptan, the half-life of sumatriptan in human subjects after subcutaneous injection of liposomal sumatriptan is predictably longer than 18.7 h.

In some aspects, migraine in accordance with the present disclosure, including episodic migraine, chronic migraine and menstrual migraine, is a multiple-attack disease. For example, episodic migraine's headache attacks occur less than 15 days per month on average and chronic migraine has a frequency of 15 or more days per month. In addition, migraine attacks are also associated with menstruation which is most likely to occur on or between 2 days before menstruation and the first 3 days of bleeding. Besides headache, migraine is often accompanied by several other symptoms including nausea, vomiting, and extreme sensitivity to light and sound. Since the plasma concentration of sumatriptan is maintained at a therapeutic concentration after the administration of liposomal sumatriptan via subcutaneous, liposomal sumatriptan may not only provide the relief of acute attack of migraine but also provide a new approach to prevent the following migraines. Based on the extended half-life, the duration of drug action after administration; a single injection of liposomal sumatriptan in the present disclosure may provide treatment of migraine or cluster headache for at least 8 hours, at least 12 hours, at least 18 hours, at least 1 day, at least 2 days, or at least 3 days.

The disclosure will be further described with reference to the following specific, non-limiting examples.

EXAMPLES

The following examples illustrate the preparation and properties of certain embodiments of the present disclosure.

Example 1 Preparation of Liposomal Sumatriptan

Liposomes were prepared by a lipid film hydration-extrusion method using repeated freeze-thawing to hydrate the lipid films. Lipids, composed of HSPC, cholesterol, and DSPE-PEG2000 (molar ratio 3:2:0.045), were dissolved in chloroform. A thin lipid film was formed by removing the organic solvent under vacuum in a rotary evaporator. For loading of sumatriptan, dry lipids were hydrated in a corresponding trapping agent, for example, 150 mM ammonium sulfate, in 9.4% sucrose solution at 60° C. for 30 min to form the MLVs. After 6 freeze-thaw cycles between liquid nitrogen and water at 60° C., MLVs were subsequently extruded 10 times through polycarbonate filter membranes with pore sizes of 0.2 µm. Unencapsulated trapping agent was removed by dialysis against 9.4% sucrose solution to form empty liposomes. Phospholipid concentration was measured using a standard phosphate assay.

A nominal drug to phospholipid ratio of 200 g/mol was designed for initial drug loading. After mixing the sumatriptan succinate (Tokyo Chemical Industry) solution with the empty liposome, the mixture was incubated at 60° C. for 30 minutes (mins). After loading, unencapsulated sumatriptan was separated by Sephadex™ G-50 Fine gel (GE Healthcare) or dialysis bag (Spectrum Labs) against a 9.4% sucrose solution to obtain purified liposomal sumatriptan. Four standard solutions of sumatriptan succinate (100, 50, 25, 12.5 µg/mL) were included to construct a standard curve. The drug concentrations of the purified liposomal sumatriptan were measured using an ultraviolet/visible (UV/Vis) spectrophotometer. Phospholipid was quantitated using a standard phosphate assay. A summary result of this purified liposomal sumatriptan is shown in Table 1, Formulation A.

Example 2 Comparison of Trapping Agents

According to the preparation method of Example 1, all liposomal sumatriptan formulations were prepared at a molar ratio HSPC/cholesterol/DSPE-PEG2000=3/2/0.45 with one or more trapping agents, (1) 150 mM of ammonium sulfate, (2) 300 mM of ammonium sulfate, (3) a mixture of 300 mM of ammonium sulfate and 0.3 mM of dextran sulfate and (4) 75 mM of triethylammonium sucrose octasulfate, respectively. To prepare different particle size of liposomes, the MLVs were either subjected a freeze-thaw cycle only or subjected a freeze-thaw cycle with an extrusion process through 0.4 µm/0.2 µm filter membrane. The Z-Ave (mean particle size) and zeta potential were measured using Zetasizer Nano-ZS90 (Malvern). Summary results of remote loading of sumatriptan with different trapping agents are shown in Table 1.

Example 3 Pharmacokinetic Study of Liposomal Sumatriptan

Jugular vein cannulated (JVC) female Sprague-Dawley rats (7-9 weeks) were used for a pharmacokinetic (PK) study. The rats were housed in a holding room which operates on a 12-hour light/12-hour dark circadian cycle with free access (ad libitum) to water and food.

Four rats (n=4) were administrated with liposomal sumatriptan (Formulation A) at the dosage of 10 mg/kg of sumatriptan tartrate by subcutaneous route. Blood samples were collected at 2, 4, 8, 24, 48 and 72 hours post-injection. Plasma samples were obtained by centrifugation and then dimethyl sulfoxide was added to the plasma samples at a final concentration of 5% (v/v) for storing the samples at −80° C. until analysis. One-hundred microliters of each sample were subject to separation of sumatriptan by a Strata C18-E tube to obtain the sumatriptan fraction and sumatriptan concentration was determined employing LC-MS/MS methods.

The unformulated sumatriptan injection was prepared by dissolving the sumatriptan tartrate in ultrapure water at 2 mg/mL. The in vivo PK profiles of the rats (n=3) administrated with unformulated sumatriptan following subcutaneous injection at the dosage of 3 mg/kg of sumatriptan tartrate were compared to the PK profiles of the rats administered 10 mg/kg of sumatriptan from the liposomal sumatriptan formulation. Blood samples were collected at 15 mins, 0.5, 1, 2, 4, 6 and 8 hours post-injection. Plasma samples were obtained by centrifugation and were kept frozen at −80° C. until analysis.

FIG. 1 depicts the mean sumatriptan concentration versus time curve over 72 hours post-injection. Table 2 provides a summary of the PK parameters which were obtained using a noncompartmental model within the PKSolver program.

TABLE 2

PK parameters derived from rats after single subcutaneous administration of liposomal sumatriptan and unformulated sumatriptan

| Parameters | Unformulated Sumatriptan | Liposomal Sumatriptan |
|---|---|---|
| n | 3 | 4 |
| Dosage (mg/kg) | 3 | 10 |
| $t_{1/2}$ (h) | 1.1 | 18.7 |
| $C_{max}$ (ng/mL) | 414 | 28.5 |
| $C_{max}$/dose | 138 | 2.9 |

TABLE 1

The drug to phospholipid(s) (D/PL) after remote loading from various formulations

| Formulation No. | Trapping Agent | Initial D/PL (g/mole) | Purified D/PL (g/mole) | Purified D/PL (mole/mole) | Z-Ave (nm) | Zeta Potential (mV) |
|---|---|---|---|---|---|---|
| A | 1 | 200 | 132.9 ± 9.4 | 0.32 ± 0.02 | 199.7[†] | −16.2[†] |
| B | 1 | 200 | 123.3[†] | 0.30[†] | 264.1[†] | −10.9[†] |
| C | 1 | 200 | 68.6[†] | 0.17[†] | 1193[†] | −12.4[†] |
| D | 2 | 200 | 150.3 ± 6.9 | 0.36 ± 0.02 | 190.2[†] | −10.6[†] |
| E | 3 | 100 | 94.9 ± 12.2 | 0.23 ± 0.03 | ND | ND |
| F | 3 | 200 | 142.4 ± 2.8 | 0.34 ± 0.01 | ND | ND |
| G | 4 | 100 | 89.1 ± 5.8 | 0.22 ± 0.01 | 192.0[†] | −14.1[†] |
| H | 4 | 200 | 176.2 ± 17.4 | 0.43 ± 0.04 | 188.5[†] | −14.0[†] |

[†]One sample for measurement;
ND, not determined.

TABLE 2-continued

PK parameters derived from rats after single subcutaneous administration of liposomal sumatriptan and unformulated sumatriptan

| Parameters | Unformulated Sumatriptan | Liposomal Sumatriptan |
|---|---|---|
| $AUC_{0-t}$ (h × g/mL) | 680.6 | 1253 |
| $AUC_{0-t}$/dose | 226.9 | 125.3 |
| $AUC_{0-inf}$ (h × ng/mL) | 687.4 | 1371.1 |

The $t_{1/2}$ was 1.1 hours for the unformulated sumatriptan group and 18.7 hours for the liposomal sumatriptan group, respectively. The $t_{1/2}$ of liposomal sumatriptan was significantly prolonged, 17-fold longer, compared with unformulated sumatriptan. The $C_{max}$ values for the unformulated sumatriptan group and the liposomal sumatriptan group were 414 ng/mL and 28.5 ng/mL, respectively. After normalization of dosage, the $C_{max}$ of the liposomal sumatriptan group was only 2.1% of the $C_{max}$ of the unformulated sumatriptan group. The $AUC_{0-t}$ values for 3 mg/kg unformulated sumatriptan and 10 mg/kg liposomal sumatriptan were 680.6 h×ng/mL and 1253 h×ng/mL, respectively. In view of $AUC_{0-t}$ after normalization by dosage, it was estimated that approximately 55% of sumatriptan released from liposomal sumatriptan and entered systemic circulation as compared to the unformulated sumatriptan group after 72 hours post-injection.

This application claims the benefit of priority to U.S. Provisional Application No. 62/608,898, filed Dec. 21, 2017, which application is hereby incorporated by reference in its entirety.

What is claimed is:

1. A method for treating migraine and/or cluster headache, which comprises:
    administering an effective amount of a sustained-release triptan composition by subcutaneous or intramuscular injection to a subject in need thereof, wherein the sustained-release triptan composition comprises:
        a liposomal triptan that has a mean particle size of not less than 100 nm and comprises one or more triptans entrapped in a liposome by ammonium sulfate,
        wherein the liposome includes sterol and one or more phospholipids, the one or more phospholipids comprising one or more phosphocholines and polyethylene glycol-phosphatidylethanolamine (PEG-PE), the sterol having a molar percentage not more than 50% based on the combination of the one or more phospholipids and sterol,
        wherein a molar ratio of the one or more triptans to the one or more phospholipids ranges from 0.15 to 0.5, and
        wherein the liposomal triptan has a zeta potential which is negative,
    whereby a sustained release profile of the liposomal triptan is demonstrated by an extended $t_{1/2}$ of triptan after administration of the sustained-release triptan composition by at least 2-fold compared with that of unformulated triptan by subcutaneous or intramuscular injection.

2. The method according to claim 1, wherein the extended $t_{1/2}$ is at least 3-fold, at least 4-fold, at least 5-fold, at least 7.5-fold, or at least 10-fold compared to that of unformulated triptan.

3. The method according to claim 1, wherein the sustained-release triptan composition is administered to a subject suffering from migraine with or without aura.

4. The method according to claim 1, wherein the sustained-release triptan composition is administered to a subject suffering from premonitory symptoms of migraine.

5. The method according to claim 1, wherein the liposomal triptan provides a sustained release of a therapeutically effective amount of the one or more triptans to the subject over a period of at least 10 hours, at least 15 hours, at least 20 hours or at least 50 hours.

6. The method according to claim 1, wherein the one or more triptans are selected from the group consisting of naratriptan, eletriptan, frovatriptan, zolmitriptan, rizatriptan, and almotriptan.

* * * * *